United States Patent
Köhler et al.

(10) Patent No.: US 7,426,257 B2
(45) Date of Patent: Sep. 16, 2008

(54) COMPUTER TOMOGRAPHY METHOD FOR A PERIODICALLY MOVING OBJECT

(75) Inventors: Thomas Köhler, Norderstedt (DE); Michael Grass, Buchholz in der Nordheide (DE); Roland Proksa, Hamburg (DE)

(73) Assignee: Koninklijke Philips electronics N.V., Eindhoven (NL)

( * ) Notice: Subject to any disclaimer, the term of this patent is extended or adjusted under 35 U.S.C. 154(b) by 343 days.

(21) Appl. No.: 10/552,399

(22) PCT Filed: Apr. 2, 2004

(86) PCT No.: PCT/IB2004/001061

§ 371 (c)(1),
(2), (4) Date: Oct. 7, 2005

(87) PCT Pub. No.: WO2004/089217

PCT Pub. Date: Oct. 21, 2004

(65) Prior Publication Data

US 2006/0203955 A1   Sep. 14, 2006

(30) Foreign Application Priority Data

Apr. 10, 2003  (EP) .................................. 03100975

(51) Int. Cl.
   *A61B 6/03*   (2006.01)
(52) U.S. Cl. ......................................................... 378/8
(58) Field of Classification Search .................. 378/4, 378/901, 8; 382/128–131
   See application file for complete search history.

(56) References Cited

U.S. PATENT DOCUMENTS 6,396,897 B1 * 5/2002 Ebrahimifard et al. ......... 378/4
6,434,215 B1 * 8/2002 Cesmeli .......................... 378/8

(Continued)

FOREIGN PATENT DOCUMENTS

DE    198 54 939 A1    6/2000

(Continued)

OTHER PUBLICATIONS

Grangeat et al., Theoretical framework for a dynamic cone-beam reconstruction algorithm on a dynamic particle model, Jul. 17, 2002, Phys. Med. Biol., 47, pp. 2611-2625.*

(Continued)

*Primary Examiner*—Chih-Cheng G Kao
*Assistant Examiner*—John M Corbett

(57) ABSTRACT

The invention relates to a computer tomography method in which a periodically moving object, in particular an organ of the body, is irradiated by a cone-shaped beam cluster (4) along a trajectory which runs on a cylindrical surface. The radiation transmitted through the object is measured by means of a detector unit (16), and at the same time the periodic movement of the object is recorded. In order to reconstruct the absorption distribution of the object, the measured values or the corresponding beams are rebinned to form a number of parallel projections, where for each of these projections a measured value is determined whose beam irradiates the object. The point in time at which this measured value was acquired is allocated to the respective projection. For the reconstruction, which may for example be carried out using a filtered back-projection, only projections whose allocated points in time lie within a predefined, specific time range (H1) within a period of the object movement are used.

11 Claims, 7 Drawing Sheets

U.S. PATENT DOCUMENTS 6,466,640 B1 10/2002 Taguchi
6,549,606 B1* 4/2003 Vaillant et al. .................. 378/4

FOREIGN PATENT DOCUMENTS

DE 101 23 979 A1 12/2002
EP 0 990 892 A2 4/2000

OTHER PUBLICATIONS

Kachelriess et al., Kymogram detection and kymogram-correlated image reconstruction from subsecond spiral computed tomography scans of the heart, Jul. 2002, Med. Phys., vol. 29, No. 7, pp. 1489-1503.*

Grass, M., et al.; 3D cone-beam CT reconstruction for circular trajectories; 2000; Phys. Med. Biol.; 45:329-347.

Kachelriess, M., et al.; Advanced single-slice rebinning in cone-beam spiral CT; 2000; Med. Phys.; 27(4):754-772.

Kachelriess, M., et al., Kymogram detection and kymogram-correlated image reconstruction from subsecond spiral CT scans of the heart; 2002; Med. Phys.; 29(7):1489-1503.

McInerney, T., et al., Deformable models in medical image analysis: a survey; 1996; Medical Image Analysis; 1(2):91-108.

Proksa, R., et al.; The n-PI-Method for Helical Cone-Beam CT; 2000; IEEE Trans. on Med. Imag.; 19(9):848-863.

Wang, G., et al.; A General Cone-Beam Reconstruction Algorithm; 1993; IEEE Trans. on Med. Imag.; 12(3):486-496.

* cited by examiner

COMPUTER TOMOGRAPHY METHOD FOR A PERIODICALLY MOVING OBJECT

The invention relates to a computer tomography method in which a periodically moving object, in particular an organ of the body, which is located in an examination area is irradiated by a cone-shaped beam cluster. The invention also relates to a computer tomography scanner for carrying out the method and to a computer program for controlling the computer tomography scanner.

Within the context of this invention, the expression "periodic movement" refers to movements in which a series of object states are repeatedly assumed by the object, always in the same sequence, during a measurement. An object state may in this case be defined, for example, by the position of the object in the examination area and the shape of the object or by a specific measured signal which is allocated to the object state. This measured signal may, for example, be the signal of an electrocardiograph if the moving object is a heart. If an electrocardiograph supplies the same measured signals at different points in time, then it is assumed that the object states at these points in time are the same. Within the context of the invention, however, the term "periodic movements" also means movements which could be referred to as "quasi-periodic" and in which object states that are repeatedly assumed by the object are not exactly identical but are substantially identical. The same applies to the time duration between two substantially identical, repeating object states, which time duration need only be substantially constant during the measurement in order to be able to refer to the corresponding movement as "periodic" within the context of this invention. Different period time durations are "substantially identical" if their time difference is small compared to the periodic time durations for the respective application. Accordingly, two object states are substantially identical if their difference is small compared to the differences which the object passes through within an entire period. Therefore, for example, movements of pulsating technical or biological objects such as organs of the body or veins may be referred to as "quasi-periodic" and hence also as "periodic". Moreover, the term "periodic movement" also encompasses attenuated oscillations or movements in which the object repeatedly assumes only some, that is to say not all, states at substantially identical time intervals.

In known methods of the type mentioned above, the spatial profile of the absorption or of the attenuation of the radiation in the periodically moving object is reconstructed from measured values acquired using a detector unit. In this case, the movement of the object leads to the measured values containing information from different object states, and this leads to movement artefacts in the reconstructed data record.

Therefore, in known reconstruction methods use is only made of measured values which have been acquired in time ranges in which the object has moved relatively little, that is to say in which the object states change only slightly. In one of these methods, the beams firstly undergo parallel rebinning in order to reduce the computational complexity. In parallel rebinning, the cone-shaped beam cluster for each radiation source position is split on the trajectory into beam fans, the beams of which in each case lie in a plane which runs parallel to the central axis of the circular or helix-like trajectory. These beam fans are then divided into groups such that each group contains only beam fans that are parallel to one another. The beam fans of a group are referred to as a projection. A point in time is allocated to each projection, said point in time being the same as the point in time at which the measured values corresponding to the central beam fan of the projection were acquired. It is assumed that all measured values of a projection were acquired at this point in time.

In the reconstruction of the absorption distribution from the rebinned beams or measured values, use is only made of projections which were acquired during predefinable time ranges in which the movement of the object is relatively small. Since—apart from in respect of the central beam fan—the point in time of a projection does not coincide with the actual acquisition time of a measured value of this projection, for the reconstruction use is frequently made of measured values whose beams do indeed come into contact with the object but were acquired at points in time which lie outside the predefined time ranges. This leads to movement artefacts which increase as the distance of the object from the central beam fan increases.

It is an object of the present invention to specify a method in which these movement artefacts are less pronounced. This object is achieved according to the invention by a computer tomography method comprising the steps using a radiation source (S) to generate a cone-shaped beam cluster (4) which passes through an examination area (13) and a periodically moving object which is located in the examination area (13), producing a relative movement between the radiation source (S) on the one hand and the object located in the examination area (13) on the other hand, where a trajectory, along which the radiation source moves relative to the object, runs on an imaginary cylindrical surface that surrounds the object, using a detector unit (16) to acquire measured values which depend on the intensity in the beam cluster (4) on the other side of the object, during the relative movement, recording the periodic movement of the object during the acquisition, reconstructing a spatial distribution of the absorption of the periodically moving object from the measured values with the aid of the recorded periodic movement of the object, comprising the steps:

a) determining the spatial area taken up by the object in the examination area (13), b) subjecting the measured values to parallel rebinning in order to form a number of groups, where the beams corresponding to the measured values of each group form beam fans (41 . . . 45) which lie in planes that are parallel to one another and to the axis of rotation, c) determining for each group a measured value whose beam irradiates the spatial area taken up by the object, and allocating to the respective group the point in time at which this measured value was acquired, d) determining those groups whose points in time, allocated in step c), lie within periodic, predefined time ranges ($H_1$), e) reconstructing the absorption distribution in the object from the measured values belonging to the groups determined in step d).

In contrast to known methods, in the invention there is determined for each group or projection a measured value whose beam irradiates the object, and the point in time at which this measured value was acquired is allocated to the projection. This leads to the time intervals between the point in time allocated to a projection and the acquisition times of said measured values of this projection, which irradiate the object, being smaller than in known methods. This reduces the incorrect use of measured values which lie outside the predefined time ranges. Since the time ranges are generally selected such that they correlate with phases of the object movement which do not contain much movement, movement artefacts are reduced.

Claim 2 describes one refinement in which the spatial area taken up by the object in the examination area is determined with a low computational complexity by reconstruction and segmentation of the object.

In Claim 3, for each group there is determined the measured value whose beam runs through the geometric center of the object. The point in time at which this measured value was acquired is allocated to the respective group. This leads to a further reduction in the incorrect use of measured values which lie outside the predefinable time range, and this further reduces the movement artefacts.

Claim 4 shows one refinement in which the periodically moving object is a heart and in which reconstructed images of a high quality can be produced inter alia with the aid of an electrocardiograph.

In claim 5, the predefinable time ranges are selected such that the object moves less in these time ranges than in other time ranges, and this leads to a further reduction of the movement artefacts in the reconstructed images.

Claim 6 defines one refinement in which the reconstruction is carried out using a filtered back-projection, and this leads to a good image quality of the reconstructed object while entailing a low computational complexity.

In claim 7 the radiation source moves relative to the examination area on a helix-like or circular trajectory, and this leads to reconstruction results with a good image quality.

A computer tomography scanner for carrying out the method is described in claim 8.

Claim 9 defines a computer program for controlling a computer tomography scanner as claimed in claim 8.

The invention will be further described with reference to examples of embodiments shown in the drawings to which, however, the invention is not restricted.

Figure 1:
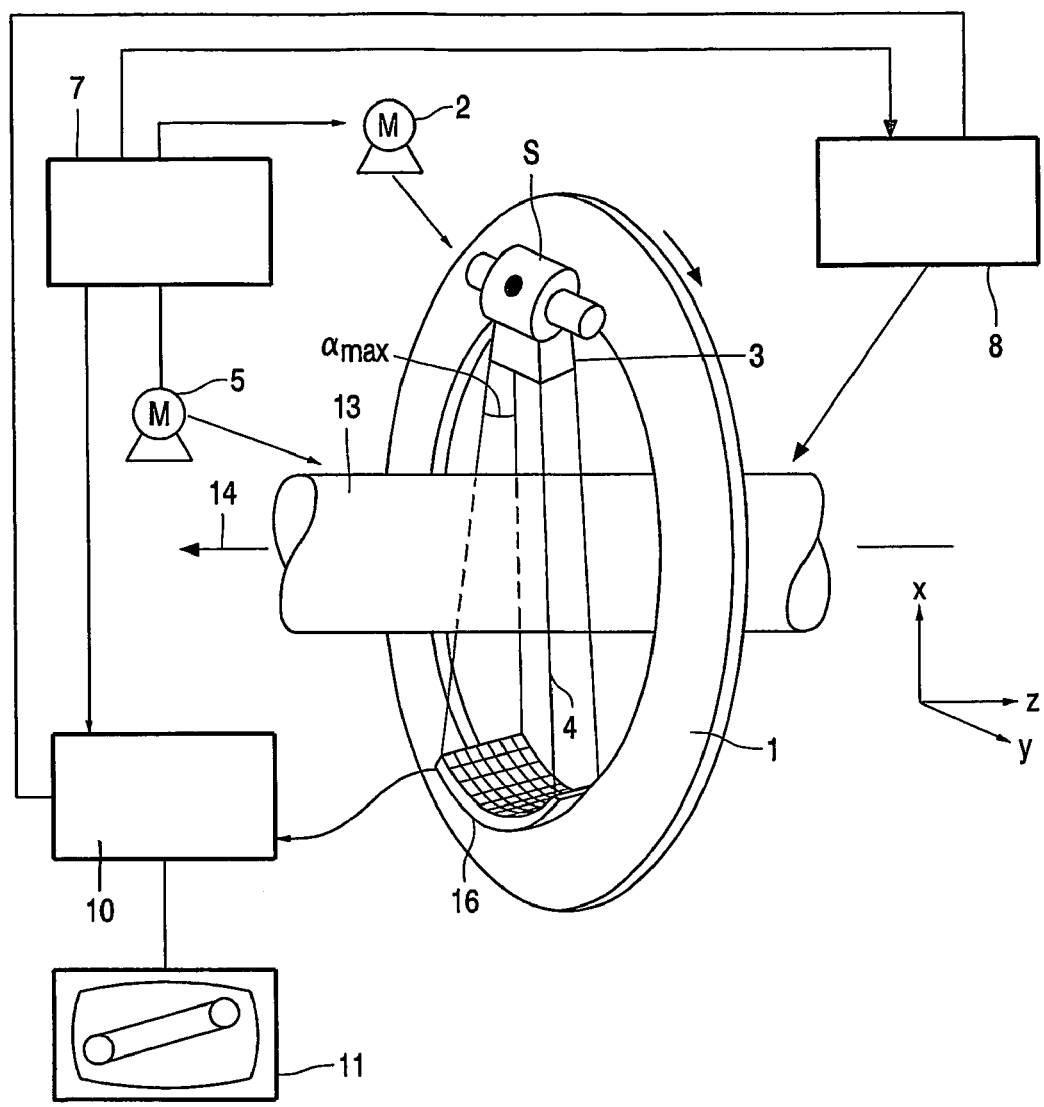
FIG. 1 shows a computer tomography scanner which can be used to carry out the method according to the invention.

The computer tomography scanner shown in FIG. 1 comprises a gantry 1 which can rotate about an axis of rotation 14 that runs parallel to the z direction of the coordinate system shown in FIG. 1. For this purpose, the gantry 1 is driven by a motor 2 at a preferably constant but adjustable angular velocity. A radiation source S, for example an X-ray generator, is attached to the gantry 1. Said radiation source is provided with a collimator arrangement 3 which masks, from the radiation generated by the radiation source S, a cone-shaped beam cluster 4, that is to say a beam cluster which has, both in the z direction and in a direction perpendicular thereto (i.e. in a plane perpendicular to the axis of rotation), a finite dimension other than zero.

The beam cluster 4 penetrates a cylindrical examination area 13 in which there is located a periodically moving object (not shown). In this example of embodiment, said object is a beating heart which carries out intrinsic movements and in some circumstances also moves back and forth on account of the patient's breathing movements. In other embodiments, other periodically moving organs of the body, such as the liver or the brain, periodically moving parts of organs of the body or periodically moving technical objects could also be irradiated.

After passing through the examination area 13, the beam cluster 4 comes into contact with a detector unit 16 which is attached to the gantry 1 and has a detector surface comprising a large number of detector elements which in this embodiment are arranged in rows and columns in the form of a matrix. The detector columns preferably run parallel to the axis of rotation 14. The detector rows are located in planes perpendicular to the axis of rotation, in this embodiment on an arc of a circle around the radiation source S (focus-centered detector). However, in other embodiments they may also be formed differently, for example describe an arc of a circle around the axis of rotation 14 or be rectilinear. Each of the detector elements with which the beam cluster 4 comes into contact supplies, in each position of the radiation source, a measured value for a beam from the beam cluster 4.

The spread angle of the beam cluster 4, designated $\alpha_{max}$, determines the diameter of the object cylinder within which the object to be examined is located during acquisition of the measured values. The spread angle is defined as the angle enclosed by a beam lying in a plane perpendicular to the axis of rotation 14 at the edge of the beam cluster 4 with a plane defined by the radiation source S and the axis of rotation 14. The examination area 13 or the object or the patient table may be moved parallel to the axis of rotation 14 or to the z axis by means of a motor 5. However, the gantry may also be moved in this direction in an equivalent manner. When a technical object is concerned rather than a patient, the object can be rotated during an examination while the radiation source S and the detector unit 16 remain stationary.

With the aid of the motors 2 and 5, the radiation source S and the detector unit 16 can describe a trajectory relative to the examination area 13, said trajectory running on an imaginary cylindrical surface. This trajectory may, for example, run in a helix-like manner when both motors are operating. If, on the other hand, the motor 5 for advance in the direction of the axis of rotation 14 is idle and the motor 2 is making the gantry rotate, the result is a circular trajectory for the radiation source S and the detector unit 16 relative to the examination area 13. In this example of embodiment, only the helix-like trajectory is considered.

During the acquisition of the measured values, the movement of the heart is recorded in a known manner by means of an electrocardiograph 8. For this purpose, the chest area of a patient is connected to the electrocardiograph 8 by way of electrodes (not shown). In other embodiments, in particular in the case of other moving objects, the movement of the object may be traced in other ways. Thus, for example, the movement information could be obtained from the values measured by the detector unit 16 themselves, so that there is no need for the movement to be recorded using an additional device, such as an electrocardiograph. For this, firstly a kymogram is produced from the measured values, from which icymogram the movement can be derived in a known manner. A detailed description of this method can be found in "Kymogram detection and kymogramn-correlated image reconstruction from subsecond spiral computed tomography scans of the heart," M. Kachelrieβ, D. A. Sennst, W. Maxlmoser, W. A. Kalender, Medical Physics 29(7): 1489-1503, 2002, to which reference is hereby made.

In this example of embodiment, it is assumed that the patient is not breathing during the measurement. The breathing movement can thus be disregarded. In other embodiments, the breathing movement could be measured, for example, using a deformable chest strap which is connected to a breathing movement measurement device.

The measured values acquired by the detector unit 16 are fed to a reconstruction and image processing computer 10 which is connected to the detector unit 16, for example via contactless data communication (not shown). Moreover, the electrocardiogram is transferred from the electrocardiograph 8 to the reconstruction and image processing computer 10. The reconstruction and image processing computer 10 reconstructs the absorption distribution in the examination area 13 and displays it on a monitor 11 for example. The two motors 2 and 5, the reconstruction and image processing computer 10, the radiation source S, the electrocardiograph 8 and the transfer of the measured values from the detector unit 16 to the reconstruction and image processing computer 10 are controlled by the control unit 7. The control unit 7 furthermore controls the transfer of the electrocardiogram from the electrocardiograph 8 to the reconstruction and image processing computer 10.

In other embodiments, the acquired measured values and the measured electrocardiograms can be fed for reconstruction firstly to one or more reconstruction computers which forward the reconstructed data e.g. via a fiberoptic cable to the image processing computer.

Figure 2:
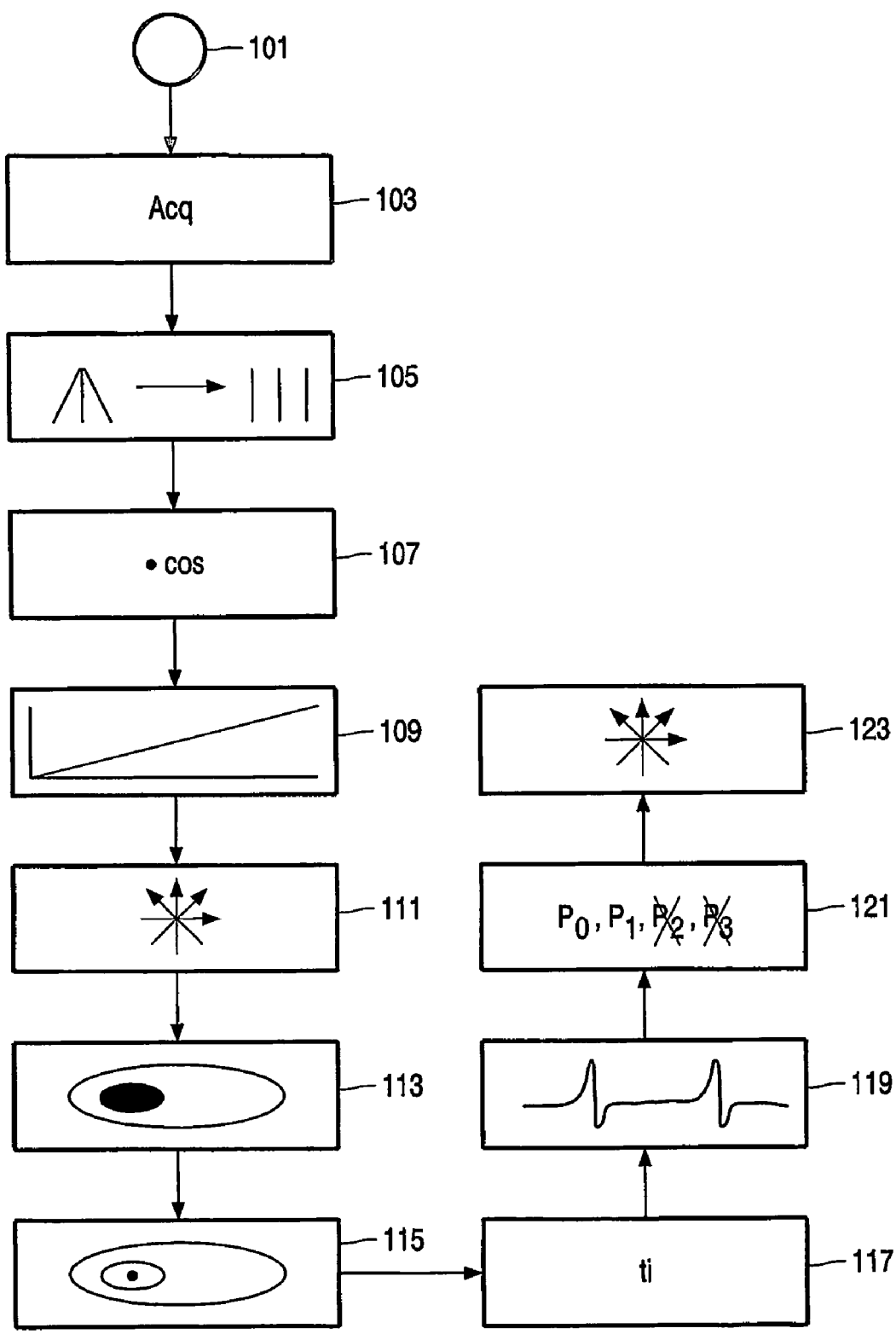
FIG. 2 shows a flowchart of the method according to the invention.

FIG. 2 shows the sequence of a measurement and reconstruction method which can be carried out using the computer tomography scanner shown in FIG. 1.

After initialization in step 101, the gantry rotates at an angular velocity which in this example of embodiment is constant. However, it may also vary, for example as a function of time or of the radiation source position.

In step 103, the examination area or the object or the patient table is moved parallel to the axis of rotation and the radiation of the radiation source S is switched on so that the detector unit 16 can detect the radiation from a large number of angular positions. At the same time as or before the switching on of the radiation source S, the electrocardiograph 8 is activated so that an electrocardiogram is measured at the same time.

Thereafter, the spatial area in which the heart is located within the examination area is determined. For this, the absorption distribution in the examination area is firstly reconstructed from the measured values at a low resolution without taking the electrocardiogram into account. There is a low resolution for example when a volume of 20×20×20 cm$^3$ is represented by 64$^3$ voxels.

In step 105, the measured values are parallel rebinned for the purposes of reconstruction. By means of the parallel rebinning, the measured values are resorted and reinterpolated as though they had been measured using a different radiation source (an expanded radiation source which is arranged on part of a helix and can emit beam fans that are in each case parallel to one another) and using a different detector (a flat, rectangular "virtual detector" including the axis of rotation 14).

Figure 3:
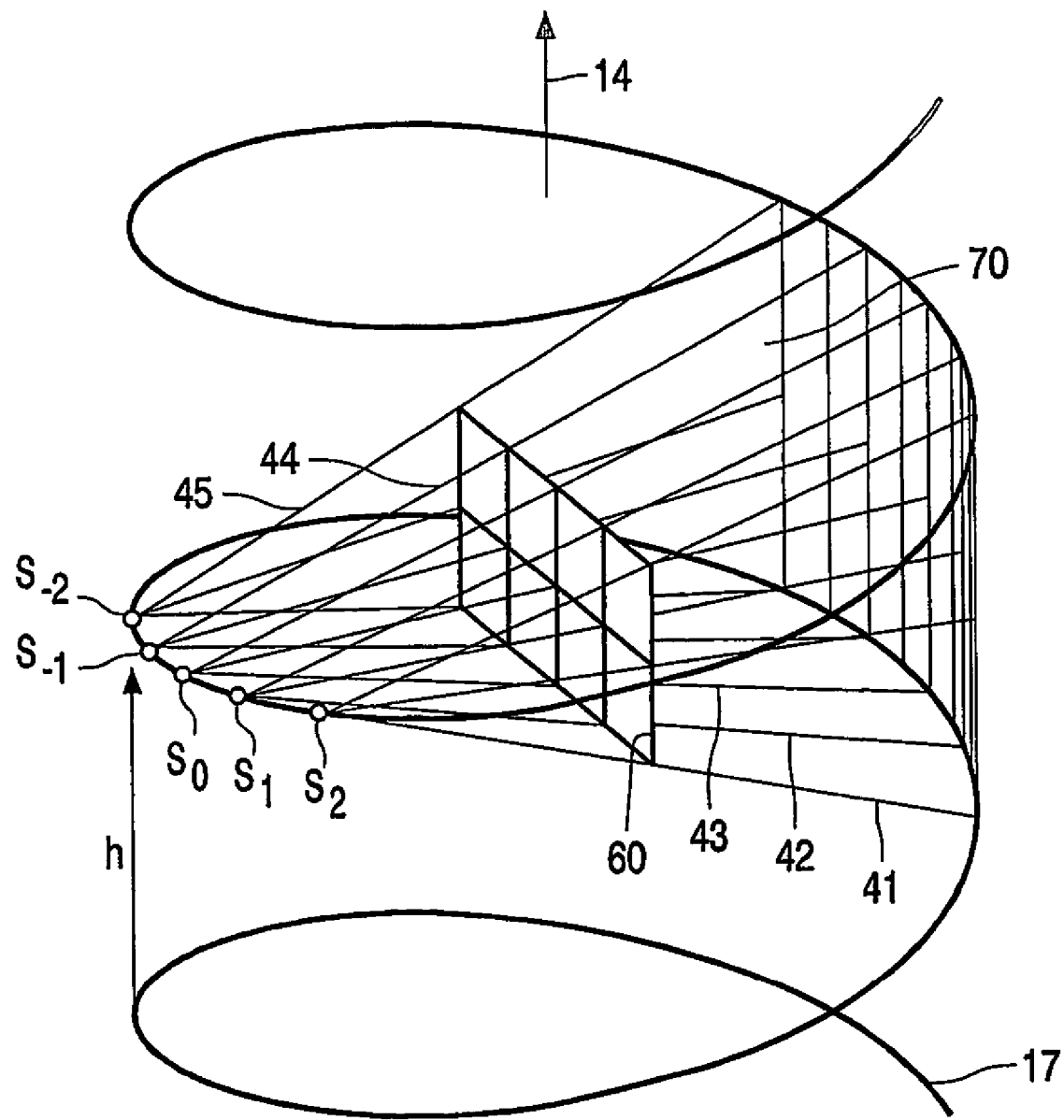
FIG. 3 shows a beam cluster of parallel rebinned beam fans.

This is explained in more detail with reference to FIG. 3. Here, 17 designates the helix-like trajectory from which the radiation source irradiates the examination area. A fan-shaped beam cluster 43, the beams of which run in a plane that includes the axis of rotation 14, is emitted from the radiation source position $S_0$. It is possible to consider that the cone-shaped beam cluster emitted from the radiation source at position $S_0$ is composed of a large number of planar beam fans which are located in planes parallel to the axis of rotation 14 and intersect at the radiation source position $S_0$. FIG. 3 shows just one of these beam fans, namely the beam fan 43.

Moreover, further beam fans 41, 42, and 44, 45 are shown in FIG. 3, said beam fans being parallel to the beam fan 43 and lying in planes that are parallel to one another and to the axis of rotation 14. The associated radiation source positions $S_{-2}$, $S_{-1}$ and $S_1$, $S_2$ are taken up by the radiation source S respectively before and after it has reached the radiation source position $S_0$.

The beam fans 41 to 45 form a group and define a beam cluster 70 with a tent-like shape. A group of beam fans is called a projection. For each projection there is then defined a rectangular, virtual detector 60 which lies in a plane that includes the axis of rotation 14 and is oriented perpendicular to the parallel beam fans of a projection. The corner points of the virtual detector 60 are the penetration points of the beams which from the outer radiation source positions come into contact with the opposite helix section, through this plane. For the beam cluster 70 in FIG. 3, S 2 and S2 are the outer radiation source positions. Detector elements that are arranged in a Cartesian manner are defined on the rectangular detector 60, that is to say rows and columns on which the measured values are reinterpolated.

Subsequently, in step 107, the measured values allocated to the individual beams are multiplied by a weighting factor which corresponds to the cosine of the cone angle of the respective beam. The cone angle of a beam is the angle encompassed by this beam with a plane oriented perpendicular to the axis of rotation 14. If said angle is small, then the cosine of the angle is essentially equal to 1, so that step 107 may be omitted.

In step 109, a one-dimensional filtering with a transmission factor that increases in a ramp-like manner with the spatial frequency is applied to the measured values.

For this, use is made of respectively successive values in the direction perpendicular to the axis of rotation 14, that is to say along a row of the virtual detector 60. This filtering is carried out along each row of the virtual detector for all groups of beam fans.

In other embodiments the parallel rebinning could be omitted. It is then known to modify the filtering since the detector unit is curved for example in the manner of an arc around the radiation source or around the axis of rotation.

Figure 4:
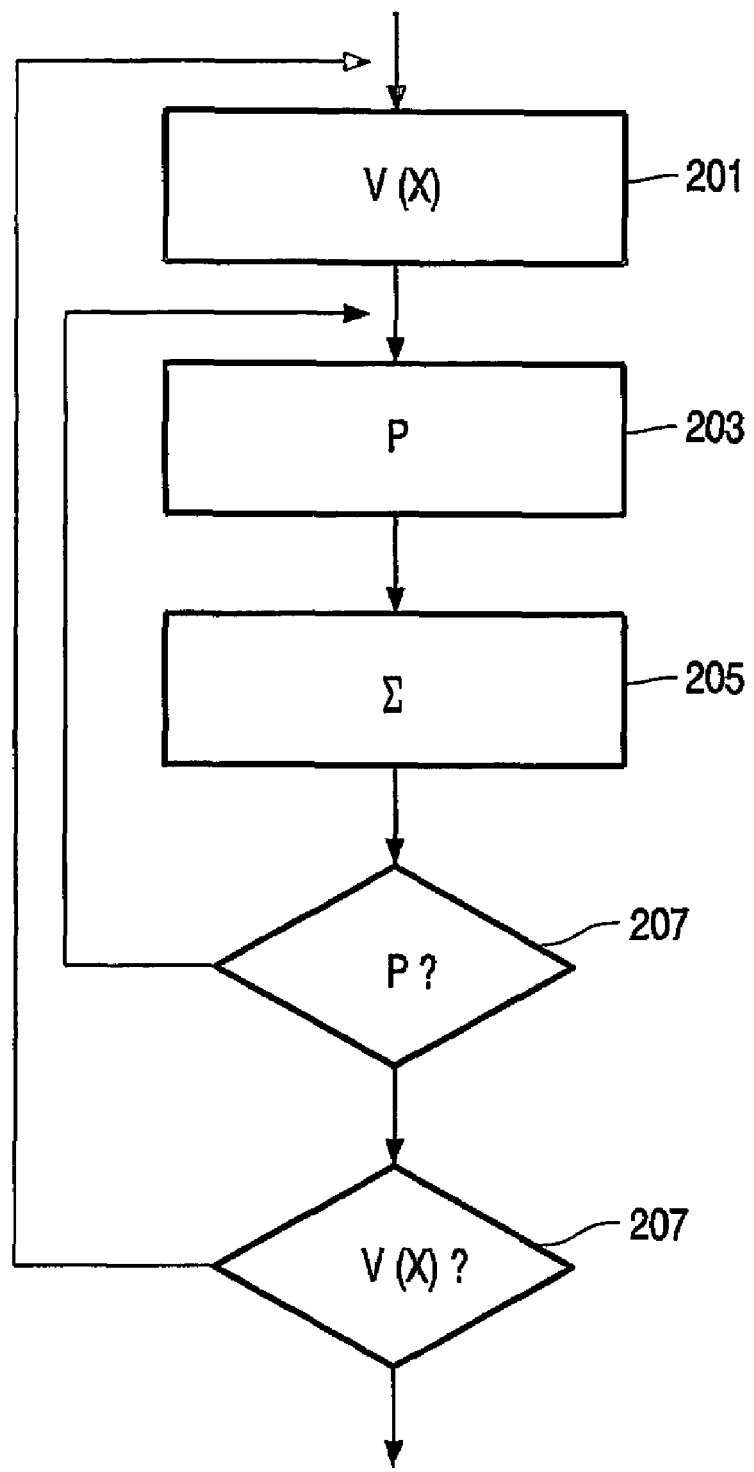
FIG. 4 shows a flowchart for a back-projection.

In step 111, the filtered measured values are then used for reconstruction of the absorption distribution in the examination area by means of a back-projection. The individual steps of the back-projection are shown in FIG. 4.

In step 201 a voxel V(x) is defined within a predefinable field of view (FOV). Since the reconstruction is to take place with a low resolution, the amount of voxels may be for example 64$^3$ and the FOV may be 20×20×20 cm$^3$. In step 203, a projection, that is to say a group of beam fans, is then selected which has not yet been used to reconstruct the voxel V(x). If no beam of the projection runs centrally through the voxel V(x), then the point at which a central beam would have come into contact with the detector surface is determined. The associated measured value is then calculated by interpolating the measured values of adjacent beams. The measured value which can be allocated to the beam of the projection that passes the voxel, or the corresponding measured value obtained by interpolation, is accumulated on the voxel V(x) in step 205. In step 207 a check is made as to whether all projections have been considered. If this is not the case, then the flowchart branches to step 203. Otherwise a check is made in step 209 as to whether all voxels V(x) in the FOV have been passed through. If this is not the case, then the method continues with step 201. If, on the other hand, all voxels V(x) in the FOV have been passed through, then the absorption in the entire FOV is determined and this reconstruction method is terminated.

In order to determine within the examination area the spatial area in which the heart is located, in the following step 113 the heart is segmented in the reconstructed three-dimensional data record.

A simple possibility for the segmentation is manual segmentation. A user, for example a physician, places markings on the surface of the heart in the three-dimensional data record. These markings are connected by lines and thus form a network that represents the surface of the heart.

A further possibility for the segmentation consists in the use of a deformable model of the heart which is moved, rotated and scaled in the data record such that the correlation between the data record and the model of the heart is maximized. This known segmentation method is explained for example in "Deformable models in medical image analysis: A survey", Medical Image Analysis, 1(2): 91-108, 1996, to which reference is hereby made.

Another known segmentation possibility is based on a region growing or region expansion process, in which a user predefines a so-called seed voxel in an object that is to be segmented, that is to say in this case in the heart. Neighboring voxels of the seed voxel are then examined using an association criterion to determine whether they do or do not belong to the heart. This association criterion may be for example the fact of whether or not they are included within a range of values of the data values of the voxel. If a data value lies within the range of values then the corresponding voxel is assigned to the heart. In the next step, the neighboring voxels of the voxel which has been newly assigned to the heart are examined with respect to the association criterion and in some circumstances also assigned to the heart. This method is repeated until no more neighboring voxels can be assigned to the heart.

The segmented heart shows the spatial area taken up by the heart in the examination area.

This determination of the spatial area taken up by the periodically moving object in the examination area represents only one embodiment. Any method which makes it possible to determine this spatial area may be used according to the invention. For instance, the examination area could also be reconstructed using other known reconstruction techniques, such as the n-PI method which is described in "The n-PI Method for Helical Cone-Beam CT", R. Proska, Th. Köhler, M. Grass, J. Timmer, IEEE Transactions on Medical Imaging, Vol. 19, 848-863, September 2000. The reconstruction could also be carried out using the method from "A General Cone-Beam Reconstruction Algorithm", G. Wang, T. H. Lin, P. C. Cheng, D. M. Shinozaki, IEEE Transactions on Medical Imaging, Vol. 12, 486-496, March 1993. The use of the reconstruction method known as ASSR (Advanced Single-Slice Rebinning) would also be possible, which although leading to poorer-quality images compared to the abovementioned reconstruction does require less computational complexity. This method is published for example in "Advanced Single-Slice Rebinning in Cone-Beam Spiral CT", M. Kachelrieβ, S. Schaller, W. A. Kalender, Medical Physics, Vol. 27, No. 4, 754-772, 2000. A reconstruction method for a circular trajectory, along which the radiation source moves relative to the object, is shown for example in "3D Cone-Beam CT Reconstruction for Circular Trajectories", M. Grass, Th. Köhler, R. Proska, Physics in Medicine and Biology, Vol. 45, No. 2, 329-347, 2000. In reconstruction to determine the spatial area taken up by the moving object, it is important that the resolution of the reconstructed three-dimensional data record is selected such that the spatial contents can be determined for example by means of known segmentation methods. This condition is met, for example, when a volume of 20×20×20 cm$^3$ is represented by $64^3$ or more voxels. Any method capable of segmenting an object in a three-dimensional data record can be used according to the invention for the segmentation.

Once the heart has been segmented in the three-dimensional data record, the geometric center of the heart can be determined in step 115 by simple geometric considerations. Only the geometric center of a known three-dimensional object is to be determined. The geometric center would be, for example, the center of gravity of this object if a spatially constant density of the object were to be assumed.

In step 117, a point in time is allocated to each projection determined in step 105. For this, it is determined which beam fan of a projection irradiates the geometric center of the heart. The point in time at which the measured values corresponding to this beam fan were acquired is allocated to the respective projection.

If in other embodiments no parallel rebinning according to step 105 has been carried out during the determination of the spatial area taken up by the periodically moving object in the examination area, then said parallel rebinning must be carried out prior to step 117.

Figure 5:
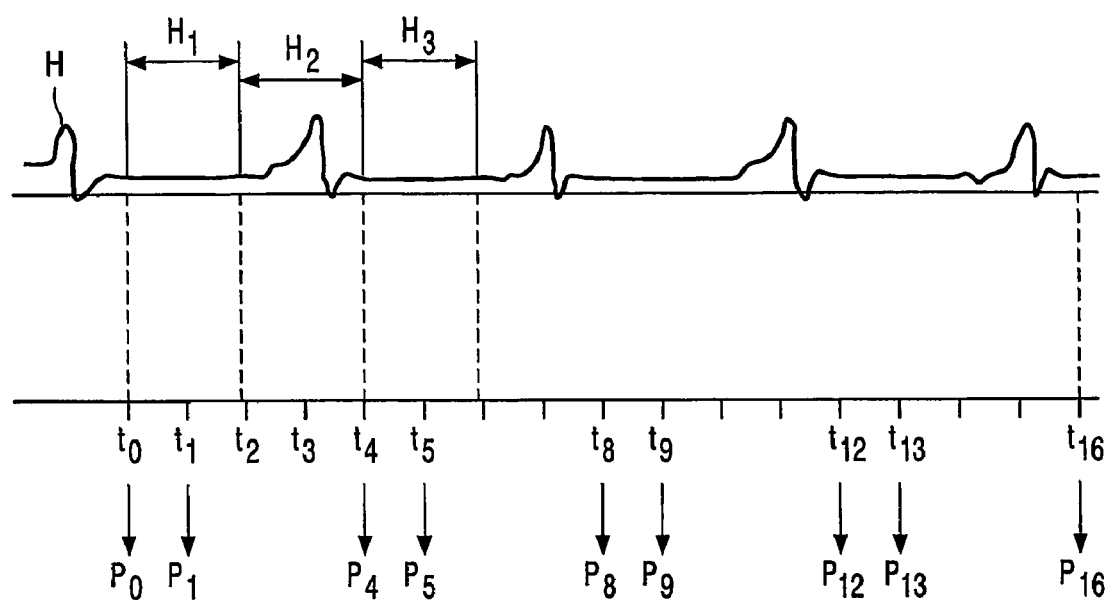
FIG. 5 shows an electrocardiogram.

For the reconstruction of the periodically moving object while talking into account the movement recorded during the measurement, repeating time ranges are selected in step 119, where the object has assumed at least a substantially identical object state in each time range. The at least one substantially identical object state thus occurs in each time range. Time ranges in which the object states assumed by the object during these time ranges differ from one another as little as possible are preferably selected. For example, two object states differ little from one another when the difference between two measured signals that characterize the respective object states, that is to say for example in the case of the heart the difference in the signals from the electrocardiograph, is small compared to the difference between the maximum and minimum value of the measured signal detected during a measurement. A difference between two measured signals is small, for example, if it is less than 1%, 2% or 5% of the difference between the maximum and minimum value of the measured signal detected during a measurement. In the reconstruction explained further below, use is only made of measured values which were acquired during these time ranges. In the case of the heart it is useful to select a time range of the diastolic phase of the movement of the heart, since in said phase the movement of the heart is considerably smaller than in the systolic phase. This is shown in FIG. 5. The period of the electrocardiogram H consists of a range $H_1$ with relatively little movement and of a range $H_2$ with a lot of movement. In this example of embodiment the time range $H_1$ is selected for the further reconstruction since in this range the object states differ less from one another than in the range $H_2$.

In step 121, those projections which were parallel rebinned in step 105 and which were acquired during the time ranges $H_1$ are determined. This is again shown in FIG. 5. In step 117, points in time $t_0$ and $t_1$ were allocated to the projections $P_0$ and $P_1$. The points in time $t_0$ and $t_1$ lie in the time range $H_1$, so that the projections $P_0$ and $P_1$ are used for the subsequent reconstruction. By contrast, projections to which the points in time $t_2$ and $t_3$ were allocated are not taken into account since the points in time $t_2$ and $t_3$ lie in the time range $H_2$.

If in other embodiments the measured values have not been multiplied according to step 107 by the cosine of the cone angle of the beam corresponding to the respective measured value during the determination of the spatial area taken up by the object in the examination area, then this can be carried out prior to the subsequent back-projection. The same applies to the filtering according to step 109.

Figure 6:
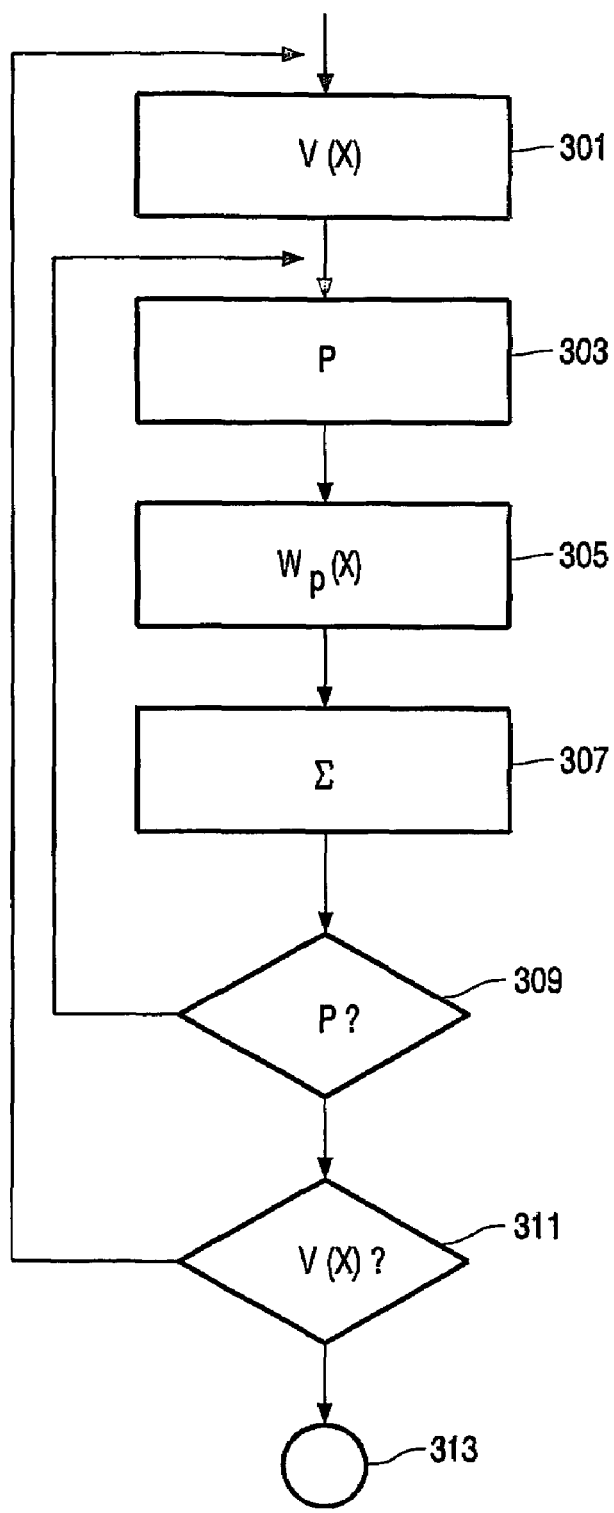
FIG. 6 shows a flowchart for a further back-projection.

The measured values of the projections determined in step 121 are then used in step 123 for the reconstruction of the absorption distribution in the heart by means of a back-projection. The individual steps of this reconstruction are shown in FIG. 6.

For this, in step 301 a voxel V(x) is determined within a predefinable field of view (FOV). The amount of voxels may be for example $512^3$ and the FOV may be $20\times20\times20$ cm$^3$. In step 303, a projection, that is to say a group of beam fans, is then selected from the projections determined in step 121, which projection has not yet been used to reconstruct the voxel V(x). If no beam of the projection runs centrally through the voxel V(x), then the point at which a central beam would have come into contact with the detector surface is determined. The associated measured value is then calculated by interpolating the measured values of adjacent beams. The measured value which can be allocated to the beam of the projection that passes the voxel, or the corresponding measured value obtained by interpolation, is multiplied in step 305 by a weighting factor $w_p(x)$. The subscript index in this case denotes the projection selected in step 303.

Figure 7:
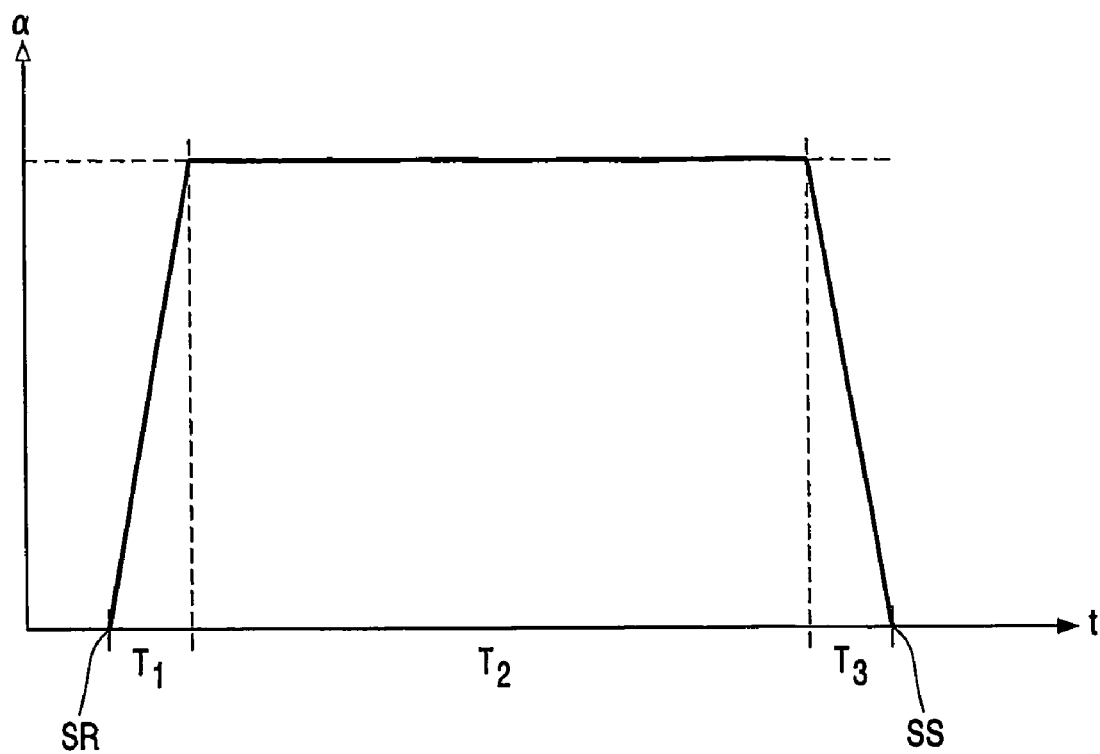
FIG. 7 shows the dependence of an $\alpha$ factor on time.

The following consideration is used to determine the weighting factor $w_p(x)$. During the acquisition, the voxel V(x) is irradiated for the first time by the cone-shaped beam cluster at a specific point in time. This point in time is referred to as the sunrise SR. The beam leaves the beam cluster again at a second point in time. This point in time is referred to as the sunset SS. A factor $\alpha_p(x)$ is then allocated to the projection selected in step 303. This factor is smaller for projections whose point in time allocated in step 117 lies relatively close to SR or SS than for projections whose corresponding point in time does not lie relatively close to SR or SS. Relatively close may mean for example that the point in time of the projection is located in a range that adjoins SR or SS, which corresponds to 5%, 10%, 15% or 20% of the overall range between SR and SS. One exemplary profile of the factor $\alpha_p(x)$ as a function of the position of the point in time of the projection between sunrise and sunset is shown in FIG. 7. In said figure, the time range between SR and SS is divided into three sections. In the first section $T_1$, which takes up 10% of the time range between SR and SS, the factor $\alpha_p(x)$ increases from SR up to a value $\alpha_c$. In the following range $T_2$, the factor is constantly equal to $\alpha_c$ and in the third range $T_3$, which also takes up 10% of the time range between SR and SS, the factor decreases again toward SS to zero.

Figure 8:
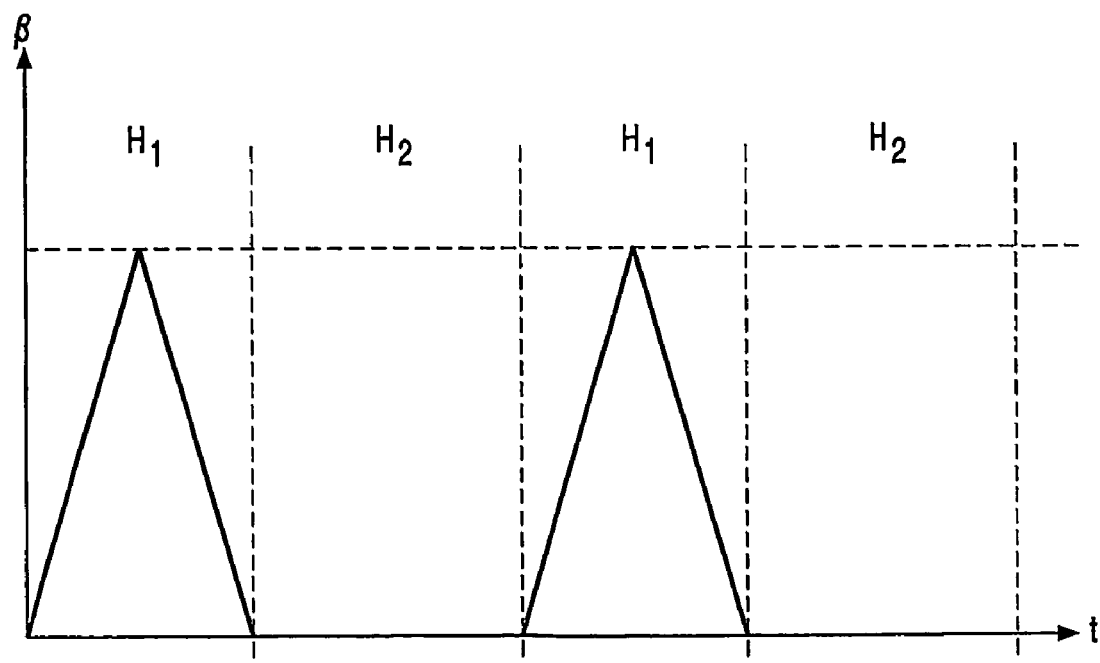
FIG. 8 shows the dependence of a $\beta$ factor on time.

It is furthermore assumed that the movement of the heart is less pronounced at a point in time which lies in the center of the time range $H_1$, which comprises little movement, than at a point in time lying closer to the boundary with the time range $H_2$, which comprises a lot of movement. Therefore, measured values of projections whose points in time lie in the center of the range $H_1$ are more highly weighted than measured values of projections whose points in time lie closer to the boundary with the time range $H_2$. In order to take this into account, a second factor $\beta_p(x)$ is assigned to the measured value. The subscript index p in this case denotes a projection and, since a point in time is allocated to each projection, also a point in time. Depending on the position of the point in time within the time range $H_1$, this factor may have a profile that ensures the following: the factor is greater for measured values of projections whose points in time lie in the center of the time range $H_1$ than for measured values of projections whose points in time lie closer to the boundary with the time range $H_2$. An exemplary profile is shown in FIG. 8.

Since the same point in time has been allocated in step 117 to all measured values whose beams belong to a projection, all measured values of a projection have the same weighting factor $w_p(x)$ for a voxel V(x), which weighting factor is defined by the following equation:

$$w_p(x) = \frac{\alpha_p(x)\beta_p(x)}{\sum \alpha_i \cdot (x) \beta_i(x)}. \qquad (2)$$

Here, $\Sigma\alpha_i(x)\beta_i(x)$ denotes a sum of all projections which have been determined in step 121 and are not redundant.

In step 307, the weighted measured value is accumulated on the voxel V(x). In step 309 a check is made as to whether all projections have been considered. If this is not the case, then the flowchart branches to step 303. Otherwise a check is made in step 311 as to whether all voxels V(x) in the FOV have been passed through. If this is not the case, then the method continues with step 301. If, on the other hand, all voxels V(x) in the FOV have been passed through, then the absorption in the entire FOV is determined and the reconstruction method is terminated (step 313).

In other embodiments, step 123 and steps 301 to 313 may be replaced by other known reconstruction methods which generate a three-dimensional data record from the parallel projections determined in step 121.

Furthermore, the reconstruction in steps 301 to 313 may be restricted to projections which are not redundant. A projection is redundant with respect to a voxel V(x) if the beam of the projection which runs through this voxel V(x) is oriented in the opposite direction with respect to a beam of another projection that has already been used to reconstruct this voxel.

The invention claimed is:

1. A computer tomography method comprising the steps:

using a radiation source to generate a cone-shaped beam cluster which passes through an examination area and a periodically moving object which is located in the examination area, producing a relative movement between the radiation source on the one hand and the object located in the examination area on the other hand, where a trajectory, along which the radiation source moves relative to the object, runs on an imaginary cylindrical surface that surrounds the object, using a detector unit to acquire measured values which depend on the intensity in the beam cluster on the other side of the object, during the relative movement, recording the periodic movement of the object during the acquisition, reconstructing a spatial distribution of the absorption of the periodically moving object from the measured values with the aid of the recorded periodic movement of the object, comprising the steps:

a) determining the spatial area taken up by the object in the examination area, b) subjecting the measured values to parallel rebinning in order to form a number of groups, where the beams corresponding to the measured values of each group form beam fans which lie in planes that are parallel to one another and to the axis of rotation, c) determining for each group a measured value whose beam irradiates the spatial area taken up by the object, and allocating to the respective group the point in time at which this measured value was acquired, d) determining those groups whose points in time, allocated in step c), lie within periodic, predefined time ranges, e) reconstructing the absorption distribution in the object from the measured values belonging to the groups determined in step d).

2. A computer tomography method as claimed in claim 1, wherein the determination of the spatial area taken up by the object, in step a), comprises the following steps:

reconstructing from the measured values a three-dimensional data record which contains the object, with a resolution which makes it possible to segment the object in the three-dimensional data record, segmenting the object in the three-dimensional data record, where the segmented object shows the spatial area taken up by the object in the examination area.

3. A computer tomography method as claimed in claim 1, wherein in step c) the geometric center of the spatial area taken up by the object in the examination area is determined and for each group a measured value is determined whose beam runs through the geometric center, where the point in time at which this measured value was acquired is allocated to the respective group.

4. The computer tomography method of claim 3, wherein the geometric center is a center of gravity of the spatial area taken up by the object in the examination area.

5. A computer tomography method as claimed in claim 1, wherein the periodically moving object is a heart, where the periodic time ranges are predefined with the aid of an electrocardiograph.

6. A computer tomography method as claimed in claim 1, wherein the object moves less in the periodic, predefined time ranges than in other time ranges.

7. A computer tomography method as claimed in claim 1, wherein the reconstruction is carried out with the aid of a filtered back-projection.

8. A computer tomography method as claimed in claim 1, wherein the relative movement between the radiation source on the one hand and the object located in the examination area on the other hand comprises a rotation about an axis of rotation and runs in a circular or helix-like manner.

9. A computer tomography scanner, in particular for carrying out the method as claimed in claim 1, comprising:

a radiation source for generating a cone-shaped beam cluster which passes through an examination area and a periodically moving object which is located therein, a drive arrangement for rotating the object located in the examination area and the radiation source relative to one another about an axis of rotation and moving them relative to one another parallel to the axis of rotation, a detector unit for acquiring measured values, said detector unit being coupled to the radiation source, a movement recording device, in particular an electrocardiograph, for recording the periodic movement of the object during the acquisition, at least one reconstruction and image processing computer for reconstructing the spatial distribution of the absorption within the examination area from the measured values acquired by the detector unit, with the aid of the periodic movement of the object recorded by the movement recording device, a control unit for controlling the radiation source, the drive arrangement, the detector unit, the movement recording device and the at least one reconstruction and image processing computer in accordance with the following steps:

using a radiation source to generate a cone-shaped beam cluster which passes through an examination area and a periodically moving object which is located in the examination area, producing a relative movement between the radiation source on the one hand and the object located in the examination area on the other hand, where a trajectory, along which the radiation source moves relative to the object, runs on an imaginary cylindrical surface that surrounds the object, using a detector unit to acquire measured values which depend on the intensity in the beam cluster on the other side of the object, during the relative movement, recording the periodic movement of the object during the acquisition, reconstructing a spatial distribution of the absorption of the periodically moving object from the measured values with the aid of the recorded periodic movement of the object, comprising the steps:

a) determining the spatial area taken up by the object in the examination area, b) subjecting the measured values to parallel rebinning in order to form a number of groups, where the beams corresponding to the measured values of each group form beam fans which lie in planes that are parallel to one another and to the axis of rotation, c) determining for each group a measured value whose beam in-adiates the spatial area taken up by the object, and allocating to the respective group the point in time at which this measured value was acquired, d) determining those groups whose points in time, allocated in step c), lie within periodic, predefined time ranges, e) reconstructing the absorption distribution in the object from the measured values belonging to the groups determined in step d).

10. A computer readable medium encoded with computer executable instructions for a control unit for controlling a radiation source, a drive arrangement, a detector unit, a movement recording device and at least one reconstruction and image processing computer of a computer tomography scanner, the computer executable instructions, when executed by a processor, cause the processor to perform the acts of claim 1.

11. The computer tomography method of claim 1, wherein in step c), the measured value for each group corresponds to a beam fan that irradiates the geometric center of the spatial area taken up by the object in the examination area.

* * * * *